United States Patent [19]

Nugent et al.

[11] Patent Number: 5,565,441
[45] Date of Patent: Oct. 15, 1996

[54] PHOSPHONOACETIC ESTERS AND ACIDS AS ANTI-INFLAMMATORIES

[75] Inventors: Richard A. Nugent, Galesburg; David J. Anderson; Stephen T. Schlachter, both of Kalamazoo, all of Mich.

[73] Assignee: The Upjohn Company, Kalamazoo, Mich.

[21] Appl. No.: 382,240

[22] Filed: Feb. 1, 1995

Related U.S. Application Data

[63] Continuation of PCT/US93/05365, Jun. 9, 1993 which is continuation of Ser. No. 926,879, Aug. 7, 1992, abandoned.

[51] Int. Cl.$^6$ .................. A61K 31/675; C07F 9/6512; C07F 9/58; C07F 9/6521
[52] U.S. Cl. ............... 514/81; 514/86; 514/89; 514/825; 544/243; 544/244; 546/22; 548/111; 548/113; 556/144; 558/179
[58] Field of Search .................. 514/86, 89, 825; 546/22; 544/243, 244

[56] References Cited

U.S. PATENT DOCUMENTS

| | | | |
|---|---|---|---|
| 3,683,080 | 8/1972 | Francis | 424/204 |
| 3,962,433 | 6/1976 | Worms et al. | 424/212 |
| 4,746,654 | 5/1988 | Brellere et al. | 514/108 |
| 5,071,840 | 12/1991 | Ebetino et al. | 514/89 |

FOREIGN PATENT DOCUMENTS

| | | |
|---|---|---|
| 5153485 | 12/1985 | Australia. |
| 0274158 | 7/1988 | European Pat. Off.. |
| 2253527 | 7/1975 | France. |
| 2310450 | 9/1974 | Germany. |
| WO93/01198 | 1/1993 | WIPO. |

OTHER PUBLICATIONS

Chemical Abstracts, vol. 103, No. 1, Abstract No. 6420d, p. 580 (1985). ZH. Obsch. Khim., Khokhlov P. S. "Diazotiazation of Alpha–Aminophosphonylacetates", vol. 54, No. 12, pp. 2785–2787 (1984).

*Primary Examiner*—Mark L. Berch
*Attorney, Agent, or Firm*—Donald L. Corneglio

[57] ABSTRACT

Compounds useful in the treatment of inflammation structurally represented as Formula I

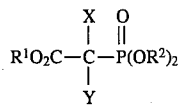

one of X or Y is H and the other is selected from the group consisting of:

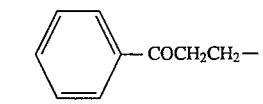

a.

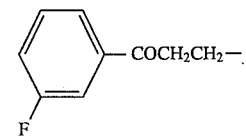

b.

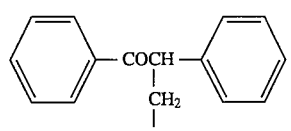

c.

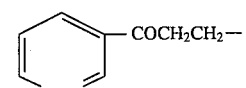

d.

ferrocenyl COCH$_2$CH$_2$—  e.

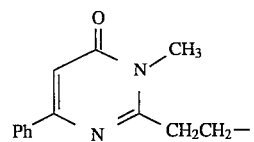

f.

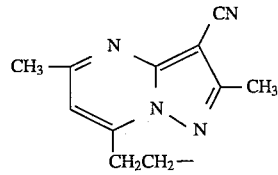

g.

or X and Y are taken together to form a ring selected from the group consisting of:

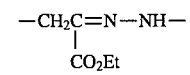

i.

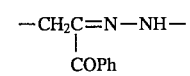

ii.

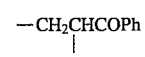

iii.

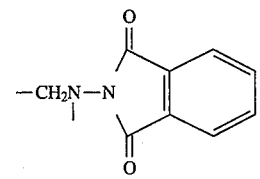

iv.

as herein defined. The compounds are useful as anti-inflammatory and anti-arthritic agents.

4 Claims, No Drawings

PHOSPHONOACETIC ESTERS AND ACIDS AS ANTI-INFLAMMATORIES

CROSS-REFERENCE TO RELATED APPLICATIONS

This application is a continuation of PCT/US93/05365, filed Jun. 9, 1993, which was a continuation of U.S. Ser. No. 07/926,879, filed Aug. 7, 1992, abandoned.

BACKGROUND OF THE INVENTION

The present invention is directed toward phosphonoacetic esters, acids, and their pharmaceutically acceptable salts which are characterized by (Formula I) and which are useful as anti-inflammatories and anti-arthritic agents.

The present compounds are useful in humans and lower animals as a safe and effective treatment of diseases characterized by abnormal phosphate and calcium metabolism, and as a treatment of inflammation. These diseases include osteoporosis, Paget's disease, periodontal disease, rheumatoid arthritis, osteoarthritis, neuritis, bursitis, soft tissue mineral disorders, ankylosing spondylitis, atherosclerosis, multiple myeloma of bone, metastatic bone disease, and mitral valve calcification. They represent a novel method of treating inflammation.

DESCRIPTION OF THE RELATED ART

For state of the art purposes, U.S. Pat. No. 4,746,654 discloses bisphosphonates useful as anti-inflammatory agents; Australian Patent A-51534/85 discloses bisphosphonates useful in treating abnormal calcium and phosphorous metabolism and useful in treating arthritis; and U.S. Pat. No. 3,683,080 discloses polyphosphonates, in particular diphosphonates useful in inhibiting anomalous deposition and mobilization of calcium phosphate in animal tissue.

PCT/US92/05398 discloses pyrazolopyrimidines and pyrimidinyl bisphosphonic esters useful as anti-inflammatories.

U.S. Pat. No. 5,071,840 discloses diphosphonic acids useful in treating abnormal calcium and phosphate metabolism.

U.S. Pat. No. 3,962,433 discloses phosphono-dicarboxylic acids useful in treating calcium metabolism disorders.

SUMMARY OF THE INVENTION

In one aspect, the present invention is phosphonoacetic esters, acids, and its pharmaceutically acceptable salts which are structurally represented by Formula I

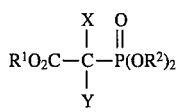

wherein $R^1$ is H, $C_1$–$C_6$ alkyl, benzyl, phenyl, phenyl (substituted with 1 to 5 F, Cl, Br, I, $NO_2$, $OCH_3$ or $C_1$–$C_4$ alkyl);

$R^2$ is H, $C_1$–$C_6$ alkyl, benzyl, phenyl, phenyl (substituted with 1 to 5 F, Cl, Br, I, $NO_2$, $OCH_3$ or $C_1$–$C_4$ alkyl), or where both $R^2$'s are taken together and form a $CH_2$—$CH_2$, $CH_2$—$CH_2$—$CH_2$ or $CH_2$—$C(CH_3)_2$—$CH_2$ to form a heterocyclic ring containing the bonded P atom and two O atoms;

one of X or Y is H and the other is selected from:

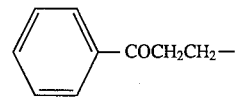
a.

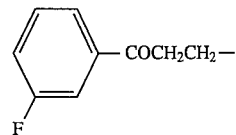
b.

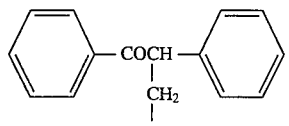
c.

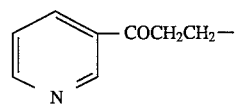
d.

ferrocenyl $COCH_2CH_2$— e.

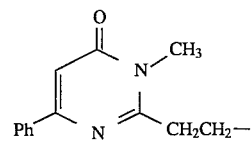
f.

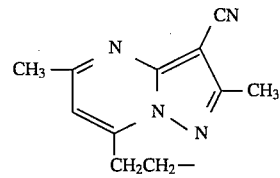
g.

or X and Y are taken together to form a ring selected from:

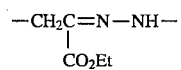
i.

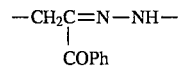
ii.

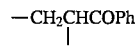
iii.

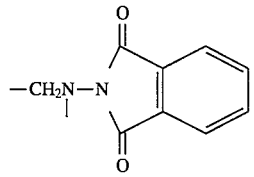
iv.

In another aspect, the present invention comprises the use of these compounds in humans and lower animals as a safe and effective treatment of chronic inflammatory diseases. These diseases include periodontal disease, rheumatoid arthritis, osteoarthritis, pneumoconioses, Crohn's disease, chronic inflammatory bowel disease, chronic asthma, atherosclerosis, multiple sclerosis, and sarcoidosis.

In yet another aspect, the invention is a method for treating inflammation by administering to an animal in need of such treatment an anti-inflammatory effective amount of a compound of Formula I. Routes of administration include oral, intramuscular, intravenous, transdermal, intra-articular, subcutaneous, or intraperitoneal. An effective amount is an amount whereby the symptoms of inflammation or arthritis such as pain and discomfort are relieved or reduced or mobility of the affected area is increased. A typical dosage is about 0.001 mg to 1.0 gram with dose determined by the particular mode of administration, use and frequency of administration.

DETAILED DESCRIPTION OF THE INVENTION

The present invention comprises phosphonoacetic esters, acids, and their pharmaceutically acceptable salts which are characterized by (Formula I, above) and which are useful as anti-inflammatories and anti-arthritic agents. These compounds are particularly useful in the treatment of arthritis and its associated symptoms such as inflammation and excessive bone growth or remodelling. In Formula I, the variable designations are further defined as follows.

The carbon content of various hydrocarbon containing moieties is indicated by a prefix designating the minimum and maximum number of carbon atoms in the moiety, i.e., the prefix $C_i$-$C_j$ defines the number of carbon atoms present from the integer "i" to the integer "j" inclusive. Thus, $C_1$-$C_3$ alkyl refers to alkyl of 1–3 carbon atoms, inclusive, or methyl, ethyl, propyl, and isopropyl.

With respect to the above, $C_1$-$C_6$ alkyl is methyl, ethyl, propyl, butyl, pentyl, hexyl, and isomeric forms thereof. The abbreviation "Ph" is used in structures and formula to mean phenyl.

The term "halo" includes fluoro, chloro, bromo and iodo.

Pharmaceutically acceptable salts means salts useful for administering the compounds of this invention or useful forms the compounds may take in vitro or in vivo and include potassium, sodium, hydrochloride, hydrobromide, hydroiodide, sulfate, phosphate, acetate, propionate, lactate, mesylate, maleate, malonate, succinate, tartrate, citric acid and the like. These salts may be in hydrated form.

The phosphonoacetic esters, acids, and derivatives (Formula I) useful as anti-inflammatories and antiarthritics are prepared as shown in Examples 1–16. Phosphonoacetates are well documented in the chemical literature and serve as useful starting materials for the Horner-Wadsworth-Emmons reaction (a modification of the Wittig reaction) in the synthesis of alkenes. See generally, A. W. Johnson in "Ylid Chemistry," Academic Press, p. 205–212 (1966); and B. M. Trost (ed.), "Comprehensive Organic Synthesis," Pergammon Press, Vol. 1, p. 761–71 (1991).

Briefly, the linear compounds are prepared via a Michael type addition reaction at −78° C. of an active methylene compound to a phosphonoacrylate. The pyrazolines are prepared via a dipolar cycloaddition of the appropriate diazo derivative to a phosphonoacrylate. The cyclopropane(s) is formed as a side product in this reaction.

The aziridine(s) is formed via nitrene addition to a phosphonoacrylate.

The corresponding phosphonic acids may be prepared by treating the ester with trimethylsilyl bromide followed by an aqueous workup.

The Formula I compounds of this invention have been tested in a Delayed Type Hypersensitivity Granuloma Assay (DTH GRA) model for inflammation. This assay is described by Dunn, C. J. et al., "Development of a delayed-type hypersensitivity granuloma model in the mouse for the study of chronic immune-mediated inflammatory disease," Agents and Actions, 27, 3/4 (1989) and "Murine Delayed-Type Hypersensitivity Granuloma," Int. J. Immunopharmc., 12, 8, 899–904 (1990).

Briefly, mBSA-sensitized mice have a DTH granuloma (DTH GRA) lesion induced by subcutaneously implanting a mBSA-soaked filter which is excised after nine days. Compounds are administered to the mice to determine their effect on the lesions. The results are recorded as percent inhibition. The larger the inhibition, the more effective the compound. Inhibition of 10 to 20% is considered to indicate anti-granuloma activity. Greater than 30% inhibition is good activity.

The DTH GRA data obtained from the compounds of Formula 1 are shown in Table 2. The compounds are scored as having anti-inflammatory activity at 10–20% inhibition and good activity at greater than 30% inhibition.

The "compound designations" correspond to the Examples' designations. The particular compounds designated are as follows

TABLE 1

| COMPOUND # | $R^1$ | $R^2$ | X | Y |
|---|---|---|---|---|
| 1 | $C_2H_5$ | $C_2H_5$ | a. | H |
| 2 | $CH_3$ | $CH_3$ | b. | H |
| 3 | $C_2H_5$ | $C_2H_5$ | c. | H |
| 4 | $CH_3$ | $CH_3$ | d. | H |
| 5 | $CH_3$ | $CH_3$ | e. | H |
| 6 | $CH_3$ | $CH_3$ | f. | H |
| 7 | $CH_3$ | $CH_3$ | g. | H |
| 8 | $CH_3$ | $CH_3$ | i. | — |
| 9 | $CH_3$ | $CH_3$ | ii. | — |
| 10 | $CH_3$ | $CH_3$ | iii. | — |
| 11 | $CH_3$ | $CH_3$ | iv. | — |
| 12 | H | $CH_3$ | f. | H |
| 13 | H | H | f. | H |
| 14 | t-butyl | $CH_3$ | b. | H |
| 15 | t-butyl | $CH_3$ | f. | H |
| 16 | H | $CH_3$ | f. | H |

TABLE 2

| Compound # | % Inhibition (10 MPK, PO) |
|---|---|
| 1 | 37 (at 50 MPK) |
| 2 | 26 |
| 3 | 21 |
| 4 | 37 |
| 5 | 32 |
| 6a | 51 |
| 6b | 37 |
| 7 | 38 |
| 8 | 59 |
| 9 | 37 |
| 10 | 47 |
| 11 | 42 |
| 15 | 21 |

EXAMPLE 1

Benzenepentanoic acid, α-(diethoxyphosphinyl)-δ-oxo-, ethyl ester Acetophenone (0.51 ml, 4.4 mmol) dissolved in THF (15 ml) was cooled to −78° C. and treated with LiHMDS (4.8 ml, 4.8 mmol). After stirring for 30 minutes, a solution of triethyl-2-phosphonoacrylate (0.94 g, 4.0 mmol) in THF (5 ml) was added. The mixture was stirred at −78° C. for 30 minutes then warmed to 0° C. for 15 minutes. Quenched with sat. $NH_4Cl$ and removed the solvents in vacuo. Dissolved the residues in ethyl acetate and washed 2×1N HCl, $H_2O$, 3× sat. $NaHCO_3$, sat. NaCl then dried over $MgSO_4$. Filtered, removed the solvent in vacuo and chromatographed the crude oil on $SiO_2$ (50 g) with 1:1 ethyl acetate/hexane. Recovered 0.85 g of a light oil (2.4 mmol, 60%) of benzenepentanoic acid, α-(diethoxyphosphinyl)-δ-oxo-, ethyl ester.

Mass Spec: m/e 356 ($M^+$), 328, 311, 237, 224, 105, 77

Infra Red: vmax ($cm^{-1}$) 1733, 1685, 1598, 1581, 1449, 1391, 1368, 1252

NMR: δ (CDCl$_3$) 7.94 (d, 2H), 7.57 (m, 1H), 7.46 (t, 2H), 4.26–4.13 (m, 8H), 3.21–3.00 (m, 3H), diastereotopic (2.42–2.31 (dt, 2H)), 1.37–1.26 (m, 12H).

EXAMPLE 2

Benzenepentanoic acid, α-(dimethoxyphosphinyl)-3-fluoro-δ-oxo-, methyl ester

Reaction of trimethylphosphonoacrylate with 3-fluoroacetophenone was carried out as follows. 3-Fluoroacetophenone (0.75 g, 5.43 mmol) was dissolved in tetrahydrofuran (10 mL), placed under nitrogen and cooled to −78° C. A solution of 1M lithium hexamethyldisilazide in THF (5.70 mL, 5.70 mmol) was added over 10–15 sec via syringe and septum. After stirring for 45 min, trimethylphosphonoacrylate (1.0 g, 5.15 mmol) was added over 30 sec. The reaction was allowed to come to ambient temperature and stirred overnight. Saturated ammonium chloride solution (10 ml) was added and most of the THF removed on a rotary evaporator. The residue was partitioned between methylene chloride (100 ml) and 1N HCl (20 ml). The organic layer was washed with water (20 ml), 5% sodium bicarbonate solution (20 ml) and brine (50 ml). The yellow solution was dried over MgSO$_4$, filtered and evaporated to yield an amber gum (1.4 g). Chromatography of the gum over silica gel (150 g, 40–60 μm) made up in 75% ethyl acetate-hexane eluted unreacted 3-fluoroacetophenone. Gradient elution with 100% ethyl acetate and then 1% methanol-ethyl acetate eluted the product over ca. 700 ml. Evaporation gave the phosphonoacetate benzenepentanoic acid, α-(dimethoxyphosphinyl)-3'-fluoro-δ-oxo-, methyl ester as a pale yellow viscous oil (730 mg, 43%).

Mass Spec: m/e 332 (2), 304 (9), 301 (12), 195 (23), 182 (66), 163 (12), 151 (15), 124 (18), 123 (100), 109 (11), 95 (25)

Infra Red: vmax 2957, 1737, 1690, 1589, 1445, 1255, 1152, 1054, 1032, 830, 783 cm$^{-1}$ NMR: δ (CDCl$_3$); 2.29–2.45 (m, 2H, CH$_2$); 2.97–3.30 (m, 3H, CH plus CH$_2$CO); 3.72–3.90 (m, 9H, 3×CH$_3$O); 7.27 (m, 1H, aromatic H$_5$); 7.45 (m, 1H, aromatic H$_4$); 7.63 (m, 1H, aromatic H$_6$); 7.74 (m, 1H, aromatic H$_2$).

EXAMPLE 3

Benzenepentanoic acid, α-(diethoxyphosphinyl)-δ-oxo-γ-phenyl-, ethyl ester

Deoxybenzoin (0.86 g, 4.4 mmol) dissolved in THF (15 ml) and cooled to −78° C. was treated with LiHMDS (4.8 ml, 4.9 mmol) then stirred for 30 minutes. A solution of triethyl-2-phosphonoacrylate (0.94 g, 4.0 mmol) in THF (5 ml) was added. After stirring for 30 minutes, the reaction mixture was warmed to 0° C. for 30 minutes. Quenched with sat. NH$_4$Cl and removed solvents in vacuo. Dissolved the residue in ethyl acetate and washed 2×1N HCl, H$_2$O, 3× sat. NaHCO$_3$, sat. NaCl then dried over MgSO$_4$. Filtered, removed solvents in vacuo and chromatographed on SiO$_2$ (50 g) with 2:3 ethyl acetate/hexane. Recovered 1.24 g of a light oil, (2.8 mmol, 72%) of benzenepentanoic acid, α-(diethoxyphosphinyl)-δ-oxo-γ-phenyl-, ethyl ester.

Mass Spec: m/e 432 (M$^+$), 387, 328, 327, 224, 105, 77

Infra Red: vmax (cm$^{-1}$) 1732, 1681, 1598, 1580, 1492, 1447, 1391, 1368, 1254, 1153

NMR: δ (CDCl$_3$) 7.93 (t, J=7.2, 2H), 7.49–7.45 (m, 1H), 7.40–7.20 (m, 7H), diastereotopic (4.74 (t, J=9.1), 4.72 (t, J=9.1), 1H), 4.29–3.97 (m, 6H), diastereotopic (3.09 (ddd, J$_{d1}$=4.7, J$_{d2}$=10.2, J$_{d3}$=23), 2.86 (ddd, J$_{d1}$=4.8, J$_{d2}$=10, J$_{d3}$=23), 1H), 2.79–2.60 (m, 1H), 2.53–2.35 (m, 1H), 1.37–1.12 (m, 9H).

EXAMPLE 4

3-Pyridinepentanoic acid, α-(dimethoxyphosphinyl)-δ-oxo-, methyl ester

The reaction of trimethylphosphonoacrylate and 3-acetylpyridine was carried out as follows. 3-Acetylpyridine (0.63 g, 5.21 mmol) was dissolved in THF (10 ml), placed under nitrogen and cooled to −78° C. A 1M solution of lithium hexamethyldisilazide in THF (5.50 ml, 5.50 mmol) was added via syringe and septum, and the cooled mixture stirred for 35 min. A solution of trimethylphosphonoacrylate (1.0 g, 5.15 mmol) in THF (3 ml) was added over 1 min. The mixture was allowed to come to ambient temperature over 3 hr when a saturated solution of ammonium chloride (10 ml) was added. Most of the THF was removed on a rotary evaporator and the residue treated with ethyl acetate (100 ml) and water (20 ml). The organic layer was washed with brine (30 ml) and dried (Na$_2$SO$_4$). Filtration and evaporation yielded an amber oil (1.2 g), which was chromatographed over silica gel (150 g, 40–60 μm). Gradient elution from 100% ethyl acetate to 4% methanol-ethyl acetate afforded the product 3-pyridinepentanoic acid, α-(dimethoxyphosphinyl)-δ-oxo-, methyl ester in the later fractions as a pale yellow oil (670 mg, 41%).

EXAMPLE 5

Ferrocene, (4-(dimethoxyphosphinyl)-5-methoxy-1,5-dioxopentyl)

The reaction of trimethylphosphonoacrylate and acetylferrocene was carried out as follows. Acetylferrocene (1.17 g, 5.13 mmol) was stirred in THF (10 ml) under nitrogen and cooled to −78° C. A 1M solution of lithium hexamethyldisilazide (5.15 ml, 5.15 mmol) in THF was added over 1 min and the reaction stirred for 30 min. A solution of trimethylphosphonoacrylate (1.0 g, 5.15 mmol) in THF (3 ml) was added and the reaction allowed to equilibrate with room temperature overnight. Saturated ammonium chloride solution (10 ml) was added and the THF removed on a rotary evaporator. Ethyl acetate (100 ml) was added and washed with water (50 ml), and brine (50 ml). After drying (Na$_2$SO$_4$), filtration and evaporation, a blood red oil (1.9 g) was obtained. Chromatography over silica (1.50 g, 40–60 μm) eluting with 1% methanol-chloroform afforded the ferrocenylphosphonoacetate ferrocene, (4-(dimethoxyphosphinyl)-5-methoxy-1,5-dioxopentyl)- as a deep red viscous oil (900 mg, 42%).

Mass Spec: m/e 423 (12), 422 (51), 358 (17), 357 (100), 267 (15), 237 (17), 219 (6), 207 (10), 189 (7), 121 (12).

Infra Red: v$_{max}$ 2955, 1736, 1666, 1455, 1257, 1053, 1029, 827 cm$^{-1}$.

NMR: δ (CDCl$_3$): 2.24–2.40 (m, 2H, CH$_2$); 2.72–2.98 (m, 2H, CH$_2$CO); 3.17–3.34 (m, 1H, CH); 3.80 (s, 3H, CO$_2$CH$_3$); 3.84 (d, J=11.0 Hz, 6H, 2×CH$_3$OP); 4.20 (s, 5H, C$_5$H$_5$); 4.45–4.54 (m, 2H, cyclopentadienyl); 4.73–4.82 (m, 2H, cyclopentadienyl).

EXAMPLE 6

(Part A):

2-Pyrimidinebutanoic acid, α-(dimethoxyphosphinyl)-1,6-dihydro-1-methyl-6-oxo-4-phenyl-, methyl ester The reaction of trimethylphosphonoacrylate and 2,3-dimethyl-6-phenylpyrimidinone was carried out as follows. 2,3-Dimethyl-6-phenylpyrimidinone (1.03 g, 5.15 mmol) was stirred under nitrogen in THF (10 ml) then cooled to −78° C. A 1M solution of lithium hexamethyldisilazide (5.50 ml, 5.50 mmol) in THF was added via a syringe and septum.

After stirring at −178° C. for 40 min, trimethylphosphonoacrylate (1.0 g, 5.15 mmol) in THF (3 ml) was added to the orange solution. The reaction was allowed to come to ambient temperature whilst stirring overnight. A saturated solution of ammonium chloride (10 ml) was added and most of the THF removed on the rotary evaporator. Ethyl acetate (100 ml) and water (20 ml) were added to the residue. The organic layer was washed with 1N.HCl (25 ml), brine (25 ml), dried (Na$_2$SO$_4$), filtered and evaporated to afford a sticky solid (1.74 g). The solid was washed from the flask with a little methyl-t-butyl ether to yield a cream solid (1.33 g, 65%). Recrystallization from acetone-hexane gave the phosphonoacetate 2-Pyrimidinebutanoic acid, α-(dimethoxyphosphinyl)-1,6-dihydro-1-methyl-6-oxo-4-phenyl-, methyl ester as translucent pale yellow crystals (1.05 g) mp 114°–5°.

EXAMPLE 6

(Part B):

2-Pyrimidinebutanoic acid, α-(dimethoxyphosphonic acid)-1,6-dihydro-1-methyl-6-oxo-4-phenyl-, methyl ester The hydrolysis of 2-Pyrimidinebutanoic acid, α-(dimethoxyphosphinyl)-1,6-dihydro-1-methyl-6-oxo-4-phenyl-, methyl ester yielded its acid derivative. The phosphonoacetate (300 mg, 0.76 mmol) was stirred in chloroform (15 ml) and trimethylsilylbromide (1.0 ml, 1.16 g, 7.58 mmol) added. The mixture was heated under reflux for 18 hours, cooled and the solvent removed to afford a glassy gum. Ethyl acetate (25 ml) and water (10 ml) were added to give an opaque mixture. Filtration of the mixture gave a gummy solid which was washed with water (10 ml). The gummy solid was dried in vacuo overnight to afford a white crusty solid mp 225°–7° as the phosphonic acid (260 mg, 93%).

EXAMPLE 7

Pyrazolo(1,5-a)pyrimidine-7-butanoic acid, 3-cyano-α-(dimethoxyphosphinyl)-2,5-dimethyl-, methyl ester The reaction of trimethylphosphonoacrylate and a pyrazolopyrimidine was carried out as follows. 2,5,7-Trimethylpyrazolo(1,5-a)pyrimidine-3-carbononitrile (0.96 g, 5.15 mmol) was stirred in pyridine (10 ml) under nitrogen and cooled in an ice-ethanol bath. A solution of 1M lithium hexamethyldisilazide (5.50 ml, 5.50 mmol) in THF was added to afford a deep red solution. After stirring for 20 min, a solution of trimethylphosphonoacrylate (1.0 g, 5.15 mmol) in THF (3 ml) was added and the mixture allowed to warm to ambient temperature over 2 hr. A saturated solution of ammonium chloride (10 ml) was added and most of the solvent removed on a rotary evaporator.

The residue was azeotroped with toluene (100 ml) and treated with ethyl acetate (100 ml) and water (50 ml). The organic layer was washed with brine (30 ml), dried (Na$_2$SO$_4$), filtered and evaporated to give a gum (1.57 g) which crystallized upon addition of methyl-t-butyl ether. The resultant solid Pyrazolo(1,5-a)pyrimidine-7-butanoic acid, 3-cyano-α-(dimethoxyphosphinyl)-2,5-dimethyl-, methyl ester (1.21 g, 62%) was recrystallized from acetone-hexane as cream crystals mp 164°–5°.

EXAMPLE 8

1H-Pyrazole-5-carboxylic-acid, 3-carboethoxy-5-(dimethoxyphosphinyl)-4,5-dihydro, methyl ester The reaction of trimethylphosphonoacrylate and ethyldiazoacetate was carded out as follows. Trimethylphosphonoacrylate (1.0 g, 5.15 mmol) was dissolved in methyl-t-butyl ether followed by ethyl diazoacetate (0.60 g, 5.26 mmol). After stirring overnight, the reaction was filtered and the resultant solid (880 mg, 55%) recrystallized from acetone-hexane to afford off-white granules of the pyrazoline 1H-Pyrazole-5-carboxylic-acid, 3-carboethoxy-5-(dimethoxyphosphinyl)-4,5-dihydro, methyl ester (699 mg) mp 100°–102°.

EXAMPLE 9

1H-Pyrazole-5-carboxylic acid, 3-benzoyl-5-(dimethoxyphosphinyl)-4,5-dihydro-, methyl ester The reaction of trimethylphosphonoacrylate and diazoacetophenone was carried out as follows. Diazoacetophenone (0.75 g, 5.14 mmol) was dissolved in methyl t-butyl ether (20 ml) followed by trimethylphosphonoacrylate (1.0 g, 5.15 mmol). After stirring at ambient temperature for 5 hr, the resultant precipitate was filtered (180 mg) and identified as the pyrazoline. Evaporation of the filtrate gave a yellow viscous oil which was placed in a refrigerator over the weekend. Attempts to dissolve this oil in a little 50% hexane-ether afforded more solid (230 mg) which was filtered and combined with the first crop (combined: 410 mg, 23%). Recrystallization from acetone-hexane gave the pyrazoline 1H-pyrazole-5-carboxylic acid, 3-benzoyl-5-(dimethoxyphosphinyl)- 4,5-dihydro-, methyl ester as white crystals (338 mg) mp 152°.

EXAMPLE 10

Cyclopropanecarboxylic acid, 2-benzoyl-1-(dimethoxyphosphinyl)-, methyl ester

The reaction mixture filtrate from Example 9 was chromatographed (SiO$_2$, 40–60 μm, 150 g) with a gradient of 25–50% acetone-hexane. The cyclopropane (60 mg, 4%) Cyclopropanecarboxylic acid, 2-benzoyl-1-(dimethoxyphosphinyl)-, methyl ester was eluted in the latter fractions as a colorless gum which slowly crystallized as a white solid mp 62°–4°.

EXAMPLE 11

2-Aziridinecarboxylic acid, 1-(1,3-dihydro-1,3-dioxo-2H-isoindol-2-yl)-2-(dimethoxyphosphinyl)-, methyl ester The oxidation of N-aminophthalimide in the presence of trimethylphosphonoacrylate was carried out as follows. N-Aminophthalimide (1.0 g, 6.17 mmol) and trimethylphosphonoacrylate (2.5 g, 12.9 mmol) were stirred in methylene chloride (25 ml) and lead tetraacetate (95%) (2.75 g, 5.89 mmol) added over 3 min. After stirring for 1 hr, the reaction was filtered and evaporated. The resultant gum was chromatographed (SiO$_2$, 500 g, 40–60 μm) eluting with a gradient of 1–4% methanol-chloroform. The aziridine was eluted in the later fractions as a yellow gum (2.84 g). A small amount of hexane was added and the gum placed in the freezer for 2 days. After removal from the freezer, crystals began to form. Filtration afforded a sticky solid which was recrystallized from acetone-hexane to yield the aziridine (780 mg, 36%). A second recrystallization gave white crystals 2-Aziridinecarboxylic acid, 1-(1,3-dihydro-1,3-dioxo-2H-isoindol-2-yl)- 2-(dimethoxyphosphinyl)-, methyl ester (680 mg, 31%) mp 123°–4°.

EXAMPLE 12

2-Pyrimidinebutanoic acid, α-(methoxyphosphinyl)-1,6-dihydro-1-methyl-6-oxo-4-phenyl 2-Pyrimidinebutanoic acid, α-(dimethoxyphosphinyl)-1, 6-dihydro-1-methyl-6-oxo-4-phenyl-, methyl ester (0.969 g, 2.46 mmol) was heated to reflux in 2N KOH (5 ml) for 20 hours. After cooling, it was diluted with water to dissolve solids and then eluted through a bed of Bio-Rad AG 50W-X4 resin (H⁺ form, 10 cm×2.5 cm² column, 200–400 mesh) with water. The sample was concentrated in vacuo: 0.84 g (2.3 mmol, 93%).

NMR: δ (CD₃OD) 8.08 (m, 2H), 7.47 (m, 3H), 6.83 (s, 1H), 3.77 (d, J=11, 3H), 3.57 (s, 3H), 3.33 (m, 1H), 3.04 (m, 2H), 2.51 (m, 2H)

EXAMPLE 13

2-Pyrimidinebutanoic acid, α-phosphon-1,6-dihydro-1-methyl-6-oxo-4-phenyl-

2-Pyrimidinebutanoic acid, α-(dimethoxyphosphinyl)-1, 6-dihydro-1-methyl-6-oxo-4-phenyl (0.403 g, 1.1 mmol) (from Example 12, above) was slurried in bromotrimethylsilane (4 ml, 30 mmol) and heated to reflux for 16 hours. Solvent was removed and the sample was dissolved in water. After stirring for 1 hour, it was partitioned between ethyl acetate and water, the aqueous layer was collected and lyophilized. The crude product was redissolved in water, and the resulting solid collected: 150 mg (0.4 mmol, 39%) mp 185°–187° C.

EXAMPLE 14

Benzenepentanoic acid, α-(dimethoxyphosphinyl)δ-oxo, dimethyl ethyl ester t-Butyl-dimethoxyphosphonoacetate (25.74 g, 0.115 mol) was dissolved in methanol (380 ml) then treated with paraformaldehyde (20.0 g, 0.670 mol) and diethylamine (14.0 ml, 0.134 mol). The reaction mixture was stirred at 22° C. for 60 hours then concentrated in vacuo. Ethyl acetate was added and washed 3×1N HCl, H₂O, 3× sat. NaHCO₃, sat. NaCl, and dried with MgSO₄. The crude methyl ether was concentrated in vacuo to recover 41.6 g of colorless oil. Phosphoric acid (85%, 1.1 ml) was added and the product distilled, t-butyl-2-(dimethoxyphosphinyl)-acrylate: 17.7 g (75 mmol, 65%) bp₀.₂ 110°–115° C.

3'-Fluoroacetophenone (1.85 ml, 15.1 mmol) dissolved in THF (25 ml) and cooled to −78° C. was treated with LiHMDS (15.4 ml, 15.4 mmol) and stirred for 30 minutes. A solution of t-butyl-2-(dimethoxyphosphinyl)-acrylate (3.56 g, 15.1 mmol) in THF (5 ml) was added, stirred for 10 minutes, then warmed to 0° C. for 2 hours. The reaction was quenched with sat. NH₄Cl, dissolved in ethyl acetate, washed 3×1N HCl, H₂O, 3× sat. NaHCO₃, sat. NaCl, dried with MgSO₄, then stripped. The sample was purified by chromatography (SiO₂, hexane/ethyl acetate): 635 mg (1.7 mmol, 63%)

NMR: δ (CDCl₃) 7.74 (d, J=7.7, 1H), 7.63 (m, 1H), 7.45 (m, 1H), 7.27 (m, 1H), 3.82 (d, J=11, 3H), 3.81 (d, J=11, 3H), 3.20–3.00 (m, 3H), 2.32 (m, 2H), 1.48 (s, 9H)

EXAMPLE 15

2-Pyrimidine butanoic acid, α-(dimethoxyphosphinyl)-1,6-dihydro-1-methyl-6-oxo-4-phenyl, dimethylethyl ester 2,3-Dimethyl-6-phenyl-pyrimidin-4(3H)-one (1.017 g, 5.08 mmol), dissolved in dry THF (10 ml) and cooled to −78° C., was treated with LiHMDS (5.3 ml, 5.3 mmol) and stirred for 30 minutes. A solution of t-butyl-2-(dimethoxyphosphinyl)-acrylate (1.14 g, 4.82 mmol) in THF (5 ml) was added, stirred for 10 minutes, then warmed to 0° C. for 30 minutes. The reaction was quenched with sat. NH₄Cl, dissolved in ethyl acetate, washed 3×1N HCl, H₂O, 3× sat. NaHCO₃, sat. NaCl, dried with MgSO₄, then stripped. The sample was purified by chromatography (SiO₂, 10% MeOH/ethyl acetate): 1.31 g. The sample solidified upon standing and was recrystallized from methyl t-butyl ether: 0.90 g (2.0 mmol, 43%) mp 94.5°–96° C.

EXAMPLE 16

2-Pyrimidinebutanoic acid, α-(dimethoxy phosphinyl)-1,6-dihydro-1-methyl-6-oxo-4-phenyl 2-Pyrimidinebutanoic acid, α-(dimethoxyphosphinyl)-1, 6-dihydro-1-methyl-6-oxo-4-phenyl, dimethylethyl ester (3.007 g, 6.89 mmol) (from Example 16, above) was heated to reflux in formic acid (55 ml) for 2 hours, then cooled and the excess solvent removed. The solid was treated with water, stirred for 1 hour, then the precipitate was filtered and dried under vacuum: 2.4 g (6.3 mmol, 91%) mp 150° C.

What is claimed:

1. A compound of Formula I or pharmaceutically acceptable salts thereof wherein Formula I is $$R^1O_2C-\underset{\underset{Y}{|}}{\overset{\overset{X}{|}}{C}}-\overset{\overset{O}{\|}}{P(OR^2)_2}$$

wherein

R¹ is H, C₁–C₆ alkyl, benzyl, phenyl, phenyl substituted with 1 to 5 F, Cl, Br, I, NO₂, OCH₃ or C₁–C₄ alkyl;

R² is H, C₁–C₆ alkyl, benzyl, phenyl, phenyl substituted with 1 to 5 F, Cl, Br, I, NO₂, OCH₃ or C₁–C₄ alkyl, or where both R²'s are taken together to form a CH₂—CH₂, CH₂—CH₂—CH₂ or CH₂—C(CH₃)₂—CH₂ to form a heterocyclic ring containing the bonded P atom and the two O atoms;

Y is hydrogen; and

X is

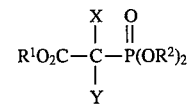   a.

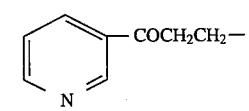   b.

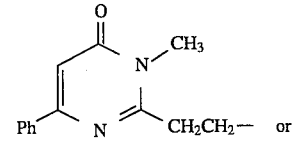   or

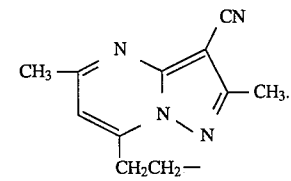   c.

2. The compound of claim 1 which is a. 3-Pyridinepentanoic acid, α-(dimethoxyphosphinyl)-δ-oxo-, methyl ester;

b. 2-Pyrimidinebutanoic acid, α-(dimethoxyphosphinyl)-1,6-dihydro-1-methyl-6-oxo-4-phenyl-, methyl ester;

c. 2-Pyrimidinebutanoic acid, α-(dimethoxyphosphonic acid)-1,6-dihydro-1-methyl-6-oxo-4-phenyl-, methyl ester;

d. Pyrazolo(1,5-a)pyrimidine-7-butanoic acid, 3-cyano-α-(dimethoxyphosphinyl)-2,5-dimethyl-, methyl ester;

e. 2-Pyrimidinebutanoic acid, α-(dimethoxyphosphinyl)-1,6-dihydro-1-methyl-6-oxo-4-phenyl;

f. 2-Pyrimidinebutanoic acid, 1,6-dihydro-1-methyl-6-oxo-4-phenyl-α-phosphono;

g. 2-Pyrimidine butanoic acid, α-(dimethoxyphosphinyl)-1,6-dihydro-1-methyl-6-oxo-4-phenyl, dimethylethyl ester; and h. 2-Pyrimidinebutanoic acid, α-(dimethoxy phosphinyl)-1,6-dihydro-1-methyl-6-oxo-4-phenyl.

3. A method for treating inflammation comprising administering an anti-inflammatory effective amount of a compound of Formula I according to claim 1 to an animal, including humans, in need thereof.

4. The method of claim 3 wherein said compound is administered to a patient in need thereof in an anti-inflammatory effective amount of from 0.001 mg to 1.0 gram and is administered orally, intramuscularly, intravenously, transdermally, intra-articularly, subcutaneously, or intraperitoneally.

* * * * *